United States Patent [19]

Detty

[11] Patent Number: 4,715,363

[45] Date of Patent: Dec. 29, 1987

[54] KNEE BRACE WITH EXTENSION ANGLE ESTABLISHING MEANS

[76] Inventor: Garnett E. Detty, 13755 E. Camino Cartamo, Tucson, Ariz. 85749

[21] Appl. No.: 912,906

[22] Filed: Sep. 26, 1986

[51] Int. Cl.[4] .............................................. A61F 3/00
[52] U.S. Cl. ..................................... 128/80 C; 623/39
[58] Field of Search ................. 128/80 C, 80 F, 80 R, 128/88; 623/39

[56] References Cited

U.S. PATENT DOCUMENTS

| | | | |
|---|---|---|---|
| 4,320,747 | 3/1982 | Daniell, Jr. ................... | 128/80 C |
| 4,370,977 | 2/1983 | Mauldin et al. ............... | 128/80 |
| 4,372,298 | 2/1983 | Lerman ........................ | 128/80 |
| 4,407,276 | 10/1983 | Bledsoe ....................... | 128/80 |
| 4,481,941 | 11/1984 | Rolfes ......................... | 128/87 |
| 4,487,200 | 12/1984 | Feanny et al. ................ | 128/80 |
| 4,493,316 | 1/1985 | Reed et al. .................. | 128/80 |
| 4,503,846 | 3/1985 | Martin ........................ | 128/80 |
| 4,523,585 | 6/1985 | Lamb et al. .................. | 128/80 C |
| 4,524,764 | 6/1985 | Miller et al. ................. | 128/80 C |
| 4,531,515 | 7/1985 | Rolfes ......................... | 128/87 |
| 4,628,916 | 12/1986 | Lerman et al. ................ | 128/80 C |

FOREIGN PATENT DOCUMENTS

| | | | |
|---|---|---|---|
| 1008446 | 5/1957 | Fed. Rep. of Germany ........ | 623/39 |
| 1187444 | 3/1959 | France ....................... | 623/39 |
| 1316572 | 5/1973 | United Kingdom ............... | 623/39 |

*Primary Examiner*—Clifford D. Crowder
*Attorney, Agent, or Firm*—Caesar, Rivise, Bernstein, Cohen & Pokotilow, Ltd.

[57] ABSTRACT

A brace for controlling the degree of motion of a person's knee. The brace includes a first cuff for releasable securement to the thigh portion of the leg and a second cuff arranged to be releasably secured to the calf portion of the leg. Elongated brace members extend between the upper cuff and the lower cuff and are interconnected by polycentric hinges. A set of pairs of wedge-like stop members are provided with the brace. Each pair of wedge members is arranged to be releasably secured to associated brace members adjacent the hinge means to serve as stop means precluding the extension of the brace beyond a maximum extension angle. Each pair of wedge members establishes a different maximum extension angle. Bands are also provided to hold the brace in place on the leg.

12 Claims, 6 Drawing Figures

KNEE BRACE WITH EXTENSION ANGLE ESTABLISHING MEANS

BACKGROUND OF THE INVENTION

This invention relates generally to orthopedic braces and particularly to braces for bone joints including means to selectively control the amount of extension that the joint is permitted to undergo when wearing the brace.

It is a common practice today to utilize orthopedic braces as a means for promoting the healing of injury to a person's bone, joint or connective tissue. Such devices provides stabilization and support to the joint during the healing process. Moreover, such devices can be used to provide stabilization or support to an otherwise healthy joint, but one subjected to various abnormal stresses, such as could occur during athletic endeavors.

Many braces are disclosed in the patent literature and many are available commercially. Examples of prior art knee other joint braces are as follows: U.S. Pat. Nos. 4,370,977 (Mauldin, et al), 4,372,298 (Lerman), 4,407,276 (Bledsoe), 4,481,941 (Rolfes), 4,487,200 (Feanny, et al), 4,493,316 (Read, et al), 4,503,846 (Martin), and 4,531,515 (Rolfes).

For many applications it is desirable to in some way limit the range of motion permitted by the brace. Typically this is accomplished by providing some type of adjustment means to limit the degree that the knee can be flexed. The patents listed above disclose various means for accomplishing the control of the range of knee movement in flexion. In addition to controlling the range of knee movement in flexion, it is also frequently desirable to provide means to control the range of knee movement in extension, that is the extent to which the knee can be straightened (the maximum angle between a longitudinal axis extending through the calf portion of the leg and a longitudinal axis extending through the thigh portion of the leg) so as to prevent hyperextension of the knee.

Heretofore, the prior art braces have not provided a simply, reliable, yet effective means for controlling the range of knee movement in extension to one of several selectable angles.

OBJECTS OF THE INVENTION

Accordingly, it is a general object of this invention to provide the knee brace which overcomes the disadvantages of the prior art.

The further object of the instant invention is to provide a knee brace which enables one to readily establish the maximum extension angle permitted by the brace.

Still a further object of the invention is to provide a knee brace which is simply in construction, easy to use and can be readily adjusted to establish a desired maximum extension angle.

SUMMARY OF THE INVENTION

Other objects and many of the attendant advantages of this invention is achieved by providing a brace for controlling the degree of motion of a bore joint, e.g., ankle, elbow, neck, etc., of a person. The brace comprises a first cuff member arranged to be releasably secured to one portion of the body of the person on one side of the joint, e.g., to the thigh portion of the leg, a second cuff member arranged to be releasably secured to another portion of the person on the other side of the joint, e.g., calf portion of the leg. A first pair of elongated brace members are mounted on opposite sides of the thigh cuff and extend downward, and a second pair of elongated brace members are mounted on opposite sides of the calf cuff and extend upward. Each brace member includes an end portion having an end face. The first and second brace members on each side of the knee brace are connected together via respective polycentric hinges. Each hinge includes one link pivotally connected between the end portion of one of the first brace members and the end portion of one of the second brace members. A set of plural pairs of stop means are provided for use with the knee brace. Each of the stop means is arranged to be releasably secured at a predetermined location to the end portion of one of the brace members to provide a respective stop surface for engaging the end face of the associated brace member pivotally connected thereto. The stop means, hinge means and the brace members cooperate with one another to enable the joint, e.g., knee, to be freely flexed, while enabling it to be freely straightened up to a maximum extension angle and no further. The maximum extension angle is established by the stop surface of the particular stop means which is utilized engaging the end face of the hingedly connected brace member. Each of the stop means when it is secured to the brace establishes a different maximum extension angle so that the wearer of the brace by selection of the appropriate stop means can fix the maximum angle that the brace will permit the joint to assume.

DESCRIPTION OF THE PREFERRED EMBODIMENT

Figures 1, 1A:
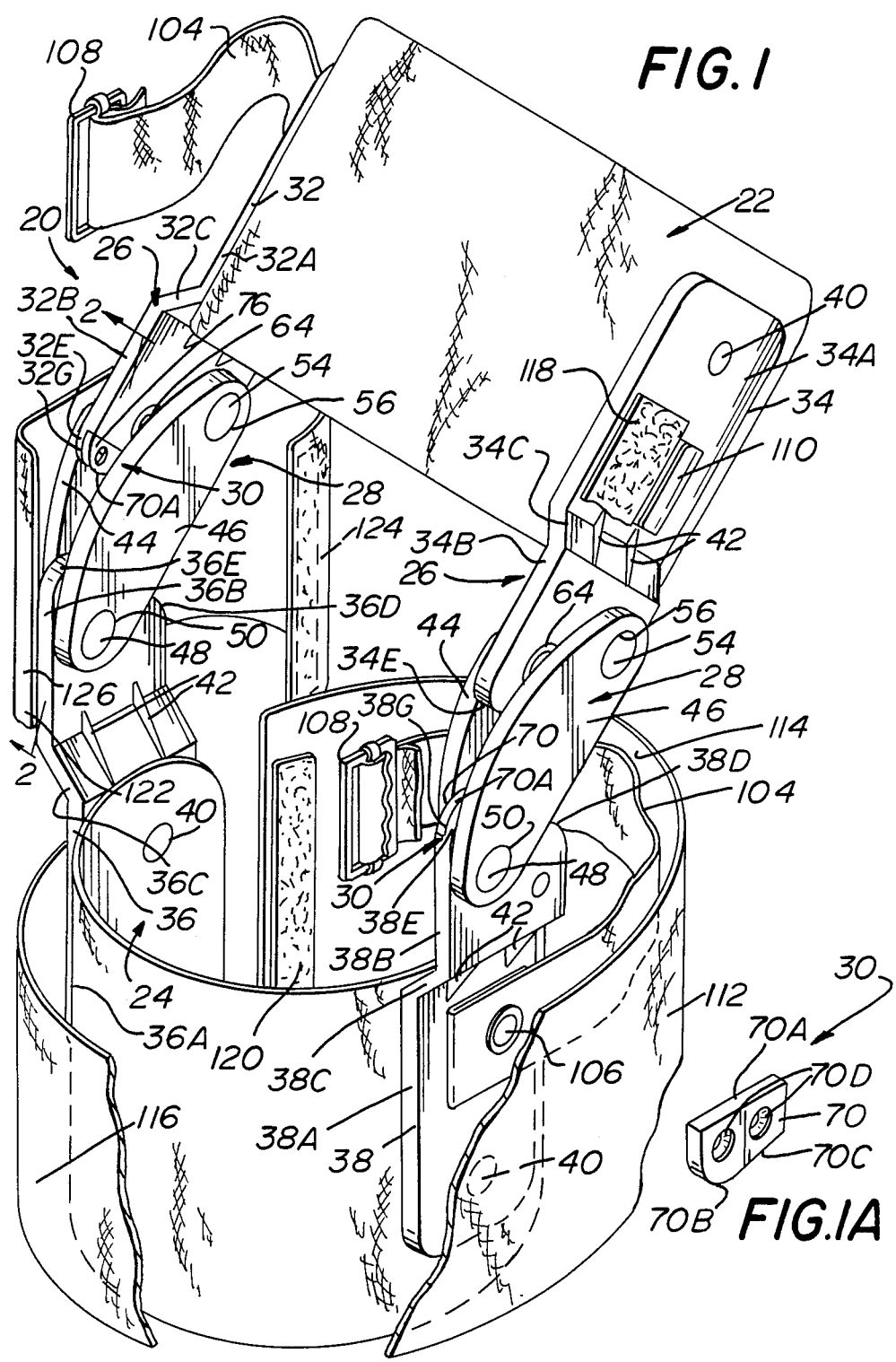
FIG. 1 is a perspective view of a portion of a knee brace constructed in accordance with the subject invention.
FIG. 1A is a perpective view of one stop member of plural stop members which can be used in the brace shown in FIG. 1.

Referring now to various figures of the drawings wherein like reference characters refer to like parts, there is shown in FIG. 1 at 20 a device or brace for controlling the degree of motion permitted by the wearer's knee, and particular the degree which the knee can be extended or straightened.

The device 20 basically comprises an upper cuff member 22 arranged to be worn on the person's leg at the thigh just above the knee and a lower cuff member 24 arranged to be worn on the person's lower leg just below the knee and opposite to the calf. Thus, each cuff member is a generally U-shaped member configured to comfortably accommodate the portion of the wearer's leg to be disposed therein. In accordance with the preferred embodiment of the invention each cuff member includes a central core, formed of a semi-rigid plastic, such as virgin vinyl, and covered on its inside and outside surfaces with a resilient material, such as a closed cell foam, or any other suitable non-allergic material. In addition, the outer surface of each of the cuff members 22 and 24 is covered by any suitable fabric such as Lycra nylon.

The two cuff members are interconnected on the medial and lateral sides thereof by respective bracing means 26 and polycentric hinge means 28. The details of those means will be described hereinafter. In accordance with this invention, the brace 20 also comprises stop means 30. The stop means 30 basically comprises a set of pairs of plural wedge-like members, the details of which will be described later. Each pair of wedge-like members is arranged to be releasably secured to the bracing means adjacent to the hinge means to establish the maximum angle to which the brace can be extended, that is straightened. Thus, each pair of wedge-like members is slightly different in construction from the other pairs to enable it to establish a respective maximum extension angle different from those established by the other pairs.

As can be seen in FIG. 1, the bracing means 26 basically comprises a pair of upper brace members 32 and 34 fixedly secured to the upper cuff member 22 and a pair of lower brace members 36 and 38 fixedly secured to the lower cuff member 24. All of the brace members are identical in construction. Therefore, only the details of brace member 32 will be described and the corresponding portions of the other brace members, as shown in the drawings, are given the same identification letter suffix as that of brace member 32.

Brace member 32 is an elongated element having a cuff-mounting portion or end 32A and a free end portion 32B. The free end portion is laterally offset from the fixed end portion by an intermediate portion 32C. Each brace member is formed of as in integral unit of a strong, yet lightweight material, such as a plastic. One particularly suitable plastic is high performance ionomer resin sold under the Trademark SURLYN by E. I. DuPont de Nemours. The cuff mounting portion 32A of brace 32 is fixedly secured, such as by plural rivets 40 to the outside surface of the upper cuff member 22 adjacent of one of its side edges. The corresponding portion of the other upper brace member 34 is fixedly secured in the same manner to the outside surface of the upper cuff member adjacent its other side edge, whereupon the two upper brace members 32 and 34 are disposed opposite one another, one on the medial side of the leg and the other on the lateral side of the leg. The brace members 36 and 38 forming the lower pair are secured in the same manner to the outside surface of the lower cuff portion 24 adjacent its side edges, so that one brace member is located on the lateral side of the leg and the outer on the medial side of the leg. The lower brace members are aligned with respective ones of the upper brace members.

In the interest of strength each of the brace members includes plural reinforcing ribs 42 on the inside and outside surfaces to the intermediate section.

The upper pair of brace members 32 and 34 are pivotably connected to the lower pair of brace members 36 and 38 via a pair of hinges 28. Each hinge 28 is of the polycentric type to enable the knee brace to bend in a manner similar to the normal articulation of the knee joint. Thus, each hinge basically comprises a pair of links 44 and 46. Each of the links is a generally elongated rigid planar member preferably formed of the same material as that of forming the brace members 32–38. The links 44 and 46 of each of the hinges are disposed on opposite sides of the upper and lower brace members connected thereby. One link is disposed on the inside surfaces of the free ends of the brace members and the other link on the outside surfaces of the free end of the brace members. Thus, as can be seen the link 44 is disposed on the inside surfaces, the free end portions 32B and 36B, of the brace members 32 and 36, while its associated link 46 is disposed on the outside surfaces of those end portions. The hinge for the other pair of brace members are disposed in a similar manner. Thus, the link 44 of the other pair of hinges is disposed on the outer surface of the free ends 34B and 38B of the brace members 34 and 38, while its associated link 46 is disposed on the inner surfaces of those free end portions.

Figure 2:
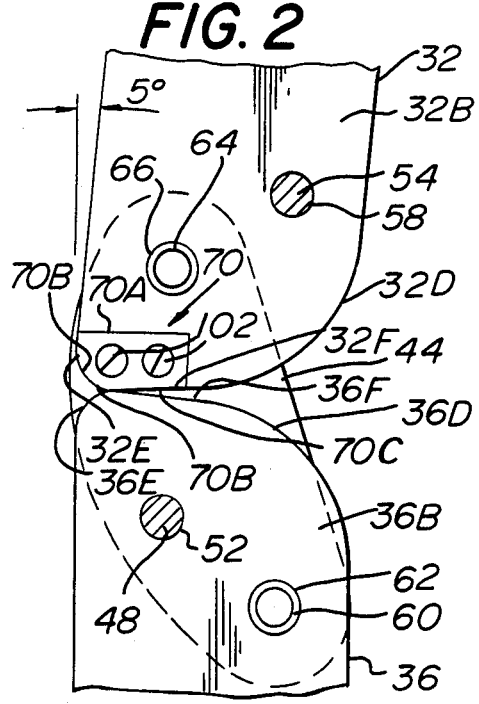
FIG. 2 is an enlarged side elevational view of the hinge portion of the brace shown in FIG. 1 and utilizing one of several stop members constructed in accordance with this invention, with said stop member establishing a maximum extension angle of 5° from full alignment.

The links 44 and 46 of each pair of hinges are pivotably connected to the free ends of their associated brace members so that an axis extending through the pivot connections for each link cross over each other in an X-type or crossing type configuration. In particular, as can be seen in FIGS. 1 and 2, one end of the link 46 is pivotably connected to the free end portion 36B of brace member 36 by a rivet 48 extending through an opening 50 in the link. The rivet is fixedly secured in an opening 52 in the free end portion 36B adjacent the front edge thereof. The other end of link 46 is pivotably connected to free end portion 32B of brace member 32 via a rivet 54 extending through an opening 56 therein. The rivet 54 is fixedly secured in an opening 58 in the free end portion 32B adjacent the rear edge thereof. One end of the link 44 is pivotably connected to the free end portion 36B of the brace member 36 by a rivet 60 extending through an opening (not shown) therein. The rivet 60 is fixedly secured in an opening 62 in the free end portion 36B of the brace member 36 adjacent the rear edge thereof. The other end of link 44 is pivotably connected to the free end 32B of brace 32 via a rivet 64 extending through an opening (not shown) therein. The rivet 64 is fixedly secured in an opening 66 in the free end portion 32B of brace member 32 adjacent the front edge thereof.

The links 42 and 46 of the other hinge member 28 are connected to the free ends of the brace members 34 and 38 in a similar manner as described with reference to the connection of brace members 32 and 36.

As can be seen clearly in FIGS. 2–5, each of the brace members includes a free end face including a large diameter radius of curvature portion contiguous with the rear edge of the brace member and a smaller radius of curvature portion contiguous with the front edge. Thus, as can be seen, in FIG. 2 the brace 32 includes the large radius free end face portion 36D contiguous with its rear edge and the smaller radius of curvature free end face portion 32E contiguous with its front edge. The portion of the free edge face intermediate portions 32D and 32E is generally linear and is denoted by the reference numeral 32F.

As will be appreciated by those skilled in the art with the links 44 and 46 mounted as described the two brace members interconnected by those links can pivot with respect to each other about a moving center of rotation or centroid, thereby replicating the bending of a knee. The free ends of the two brace members joined by each of the hinges 28 are spaced sufficiently from each other so that the brace can be bent freely without those adjacent surfaces engaging. Thus, the brace 20 doesn't provide any impediment to full flexion of the knee, that is, the knee can be bent to the maximum angle permitted by the wearer's anatomy.

Figure 3:
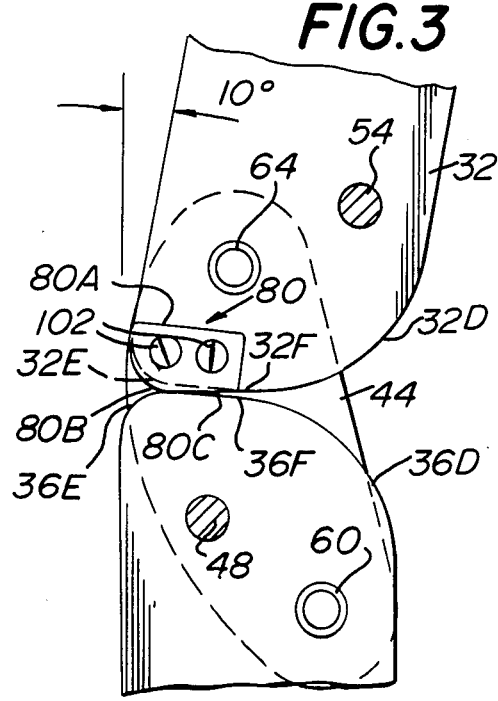
FIG. 3 is a view similar to that of FIG. 2 but showing a stop member establishing a maximum angle of 10° from full alignment.
Figure 4:
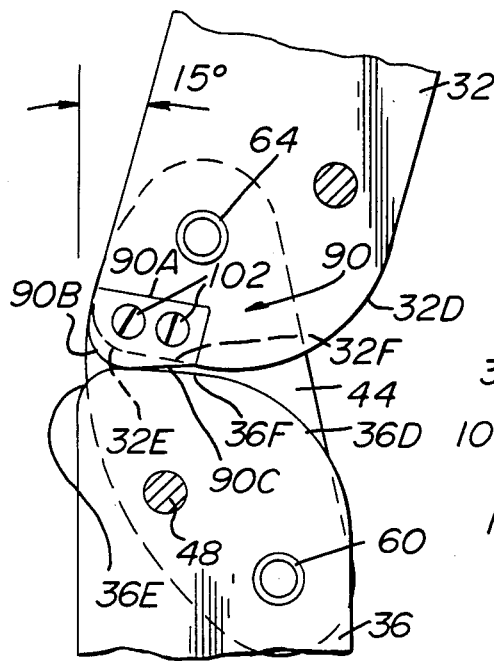
FIG. 4 is a view similar to that of FIG. 3 but showing a stop member establishing a maximum angle of 15° from full alignment.
Figure 5:
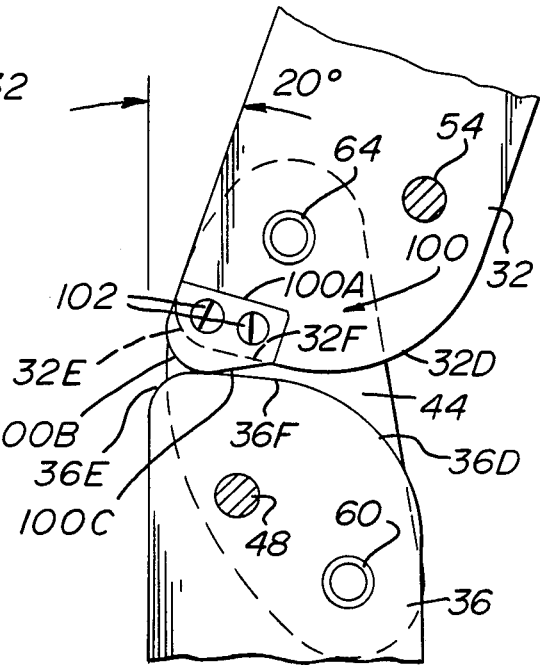
FIG. 5 is a view similar to that of FIG. 4 but showing a stop member establishing an angle of 20° from full alignment.

As mentioned earlier, respective pairs of wedge members form the stop means 30. Any pair of wedge members can be secured to the brace 20 to prevent extension of the brace member beyond a predetermined angle from full extension (that is 180° longitudinal axial alignment of the brace members). In particular and in accordance with the preferred embodiment of this invention, the stop means 30 comprises a set of four pairs of wedges 70, 80, 90 and 100 establishing maximum extension angles of 175° (5° from full extension as shown in FIG. 2), 170° (10° from full extension as shown in FIG. 3), 165° (15° from full extension as shown in FIG. 4), and 160° (20° degrees from full extension as shown in FIG. 5), respectively. Irrespective of which pair is used, one wedge member of each pair is arranged to be releasably secured to one brace member at each hinge to act as a stop by engaging a cooperating surface of the associated brace member. In particular, when so mounted, each wedge member forms a stop surface which is arranged to engage or contact the end face of the opposed brace member to preclude the brace from pivoting about its hinge beyond the point at which contact is made.

In the exemplary embodiment shown herein the wedge members are secured to the respective end portions of diagonally opposed brace members 32 and 38. However, those wedge members can be secured to the respective end portion of the diagonally opposed brace members 34 and 36 or can be secured to the respective end portions of either of the upper brace members 32 and 34 or the lower brace members 36 and 38, if desired, by providing suitable mounting means on the desired brace members. In any event, the mounting means for the wedge members comprise recesses in the brace members and threaded fastening means for holding the wedges in place therein. Thus, in the embodiment shown herein the diagonally opposed brace members 32 and 38 include respective recesses 32G and 38G in their end portions 32B and 38B, respectively. The recesses are located on the inside surfaces of the brace members and each is shaped to accommodate any of the wedge members 70, 80, 90 or 100 making up the stop means 30.

As can be seen in FIGS. 1A, and 2-5, the wedge members 70, 80 and 90 include base surfaces 70A, 80A, 90A, 100A, respectively. These surfaces are arranged to engage a flat base wall or ledge at the bottom of the brace member's wedge mounting recess. Disposed opposite of the base surface of each wedge member is the heretofore mentioned stop or engaging surface. Thus, each wedge 70 includes a stop surface made up of an arcuate portion 70B and a merging linear portion 70C. The stop surfaces of wedge 70 (that is, portions 70B and 70C) coincide with the end faces portion 32E and 32F of brace member 30 and with the end faces 38E and 38F of the brace member 38. Accordingly, when a pair of wedges 70 are mounted on the brace 20 the stop surfaces of those wedges engage the end surfaces or faces of the associated brace members to prevent the brace 20 from extending beyond 175° (as shown in FIG. 2). The wedge members 80 each include a stop surface made up of arcuate surface 80B and merging linear surface 80C. The radius of curvature of surface 80B of wedge 80 is larger than that of surface 70B of wedge 70 so that the stop surface of wedge 80 extends beyond the end face 32E of brace member 32 and beyond the end face 38E of brace member 38. Accordingly, the stop surfaces of the wedges 80 engage the end surfaces or faces of the associated brace members at a closer point, thereby preventing the brace from extending beyond 170° (as shown in FIG. 3). The wedge members 90 each include a stop surface made up of an arcuate portion 90B and a merging linear portion 90C. The radius of curvature of portion 90B of wedge 90 is larger then the radius of curvature of portion 80B of wedge 80 so that the stop surface of wedge 90 extends further beyond the end face 32E of brace 32 and 38E of brace member 38. Accordingly, the stop surfaces of the wedges 90 engage the end surfaces of the brace members 34 and 36 at an even closer point to prevent the brace 20 from extending beyond 165° (as shown in FIG. 4). Each of the wedge members 100 also includes a stop surface made up of an arcuate portion 100B merging into a linear portion 100C. The radius of curvature of portion 100B of wedge 100 is larger then the radius of curvature of portion 90B of wedge 90 so that the stop surface of wedge 100 extends even further beyond the end face 32E of brace member 38E of brace member 38. Accordingly, the stop surfaces of the wedges 100 engage the end face of the brace members 34 and 36 at an even closer point to prevent the brace 20 from extending beyond 160° (as shown in FIG. 5).

In the interest of enabling the brace to be set up to establish the maximum extension angle, that is to customize the brace for the particular wearer, the wedge member's 70, 80, 90 and 100 each are arranged to be releasably secured in their respective mounting recess. The means for effecting such releasable securement comprise a pair of threaded fasteners or screws 102 which extend through countersunk holes 70D in the wedge member 70 and through corresponding holes in the wedges 80, 90 and 100. The screws 102 terminate in threaded openings, not shown, in the free end of the brace portion having the wedge mounted recess therein. Thus, if it is desired to change the maximum extension angle that the brace will permit, all that is required is to unscrew the pair of screws 102 from each wedge, to replace the wedge in the recess by another wedge and thereafter to screw the replacement wedge in place.

In order to expedite the mounting of the brace on the person's knee, the brace 20 includes a pair of elastic straps 104, one connected to the upper cuff member 22 and the other to the lower cuff member 24. In particular, one elastic strap 104 is fixedly secured at one end thereof to brace portion 32A on the upper cuff member 32 via a rivet 106 and the other elastic strap is connected to brace portion 38A via rivet 106. Each strap 104 is preferably formed of an elastic material and includes at its free end a conventional buckle 108. The buckle of the upper strap is arranged to be received in a clasp 110 mounted on the brace portion 34A at the other side of the upper cuff member 22 to enable the strap to encircle the back of the wearer's thigh to hold the upper cuff on the thigh in place. The buckle 108 of the lower strap is received in a similar clasp (not shown) mounted on brace portion 36A to enable the lower strap to encircle the back of the wearer's calf to hold the lower cuff in place.

The straps 104 only serve as temporary means to hold the brace in place while it is being secured to the wearer's leg. Thus, the principle means of securing the brace to the leg comprise a pair of relatively wide bands 112. One band is for wrapping around the upper leg at the upper cuff and the other is for wrapping around the lower leg at the lower cuff. In the interest of drawing simplicity, the lower band 112 is shown. As can be seen, each band 112 is an elongated member formed of an elastic material and having a rubberized inner surface 114, and a nappy outer surface 116. The outer surface is suitable for engagement with the "hook type" components of a Velcro ® type fastener component. The inner surface of each band includes at each end thereof a strip 118 of the hook-type Velcro ® component. In order to enable the band 112 to be secured to their respective cuff members, a strip 118 of the nappy or loop-type Velcro ® component is fixedly secured to the brace portion 34A and a similar strip 118 is fixedly secured to the brace portion 32A. The "hook-type" strip 120 on one end of the inside surface of one band 112 is brought into engagement with the strip 118 and the strap wrapped around the wearer's thigh at the upper cuff so that the hook-type patch 120 at the free end of the band 112 engages the underlying nappy surface 114 of the band 112 to hold the band in place. The lower band 112 is wrapped about the lower cuff in a similar manner.

As can be seen in FIG. 1, a pair of elastic protective pads 122 (only one of which is shown) are provided to encircle the free ends of the linked brace members and their interposed hinges to complete the brace 20. Each pad, 122 is constructed similarly to the bands 112 but is substantially shorter in length and includes a strip 124 of the hook-type Velcro ® fastening element on the inner surface thereof. That Velcro ® fastening element is arranged to engage the nappy outer surface 126 of the pad when the pad is wrapped around the end of the brace members and the interposed hinge. The pads 120, like the bands 112, are cushioned so that when each pad is in place there are no exposed hard surfaces of the brace means or hinges to contact the leg of the wearer.

As should be appreciated by those skilled in the art, the subject invention is applicable to other bone joints of a person's body, such as the elbow, ankle, and even the neck, in order to prevent hyperextension thereof. Hence, the subject invention can be configured for any particular joint application.

Without further elaboration, the foregoing will so fully illustrate my invention that others may, by applying current or future knowledge, readily adopt the same for use under various conditions of service.

I claim:

1. A brace for controlling the degree of motion of a bone joint comprising a first cuff member arranged to be releasably secured to a portion of the person's body on the side of said joint, a second cuff member arranged to be releasably secured to a portion of the person's body on the other side of said joint, a pair of elongated first brace members extending on opposite sides of said first cuff member, a pair of elongated second brace members extending on opposite sides of said second cuff member, each of said brace members having an end portion including an end face, and wherein the end face of one of said first brace members includes a recess therein and wherein the end face of one of said second brace members includes a recess therein, first hinge means including a link connected between the end portion of one of said first brace members and the end portion of one of said second brace members and second hinge means including a link connected between the end portion of the other of said first brace members and the end portion of the other of said second brace members, together forming a polycentric hinge, and a plural stop means each in the form of a respective insert having a peripheral stop surface and wherein anyone of said stop means being selected for releasable securement in one of said recesses whereupon its stop surface forms the end face of the brace member to which it is secured, and which stop surface is arranged to engage the end face of the brace member hingedly connected thereto, said selected stop means, hinge means and brace members cooperating with one another to enable the person's joint to be straightened up to a maximum angle and no further, said maximum angle being established by the stop surface of said selected stop means engaging the end face of the brace member hingedly connected thereto, each of said plural stop means being arranged when secured to said brace member to establish a different maximum angle, whereupon said person can, by the selection of the appropriate stop means, fix the maximum angle that the brace will enable the joint to assume.

2. The brace of claim 1 wherein each of said inserts is a wedge-like member whose stop surface is arcuate.

3. The brace of claim 2 wherein said insert is arranged to be releasably secured in said recess via threaded fastening means.

4. The brace of claim 1 wherein said stop means are provided in pairs of stop members, the stop members in each pair being identical, and with one stop member of a selected pair of stop members being releasably secured in the recess in one of said first brace members and with the other of said stop members of said selected pair being releasably secured in the recess in one of said second brace members, whereupon said stop members provide respective stop surfaces engaging the end faces of the respective brace members pivotably connected thereto.

5. The brace of claim 1 wherein said brace means and said stop means are formed of a plastic material.

6. The brace of claim 1 wherein said cuffs are each shaped to readily accommodate the respective portion of the body of the person adjacent said joint.

7. The brace of claim 6 additionally comprising means to hold said cuff members in place on the body of the person.

8. The brace of claim 1 wherein each of said hinges is a polycentric hinge.

9. The brace of claim 8 wherein said first hinge means includes a first link pivotably connected at one point to the end portion of said one of said first brace members and pivotably connected at a second point to the end portion of said one of said second brace members, and second link pivotably connected at a third point to the end portion of said one of said first brace members and pivotably connected at a fourth point to the end portion of said one of said second brace members.

10. The brace of claim 9 wherein said second hinge means also comprises first and second links pivotably connected to the other two brace members in the same manner as said first hinge means is connected to its brace members.

11. The brace of claim 10 wherein said brace means and said stop means are formed of a plastic material.

12. The brace of claim 11 additionally comprising means to hold said cuff members in place on the body of the person.

* * * * *